United States Patent [19]

Muxfeldt et al.

[11] 3,947,517

[45] Mar. 30, 1976

[54] STEREOSELECTIVE INTRODUCTION OF TETRACYCLINES HYDROXYL GROUP AT 12(a) POSITION IN SYNTHESIS OF TETRACYCLINES

[75] Inventors: Hans H. Muxfeldt, Ithaca, N.Y.; Jeffrey Michael, Braunschweig, Germany

[73] Assignee: Research Corporation, New York, N.Y.

[22] Filed: Dec. 29, 1972

[21] Appl. No.: 319,486

Related U.S. Application Data

[63] Continuation of Ser. No. 832,680, June 17, 1969, abandoned.

[52] U.S. Cl. 260/559 AT; 260/240 F; 260/306.7 R; 260/340.6; 260/473 F; 260/482 R; 260/483; 260/590 FB

[51] Int. Cl.² ......................................... C07C 103/19

[58] Field of Search ............................. 260/559 AT

[56] References Cited
UNITED STATES PATENTS 3,188,348   6/1965   Butler et al.................. 260/559 AT

*Primary Examiner*—Donald G. Daus
*Assistant Examiner*—Anne Marie T. Tighe
*Attorney, Agent, or Firm*—Brumbaugh, Graves, Donohue & Raymond

[57] ABSTRACT

In the synthesis of tetracyclines, a critical step is the stereospecific or stereoselective introduction of a hydroxyl group at the C-12(a) position, a novel method for the introduction of this critical hydroxy group is disclosed. Additionally, synthetic procedures for obtaining tetracycline precursors are discussed.

9 Claims, 3 Drawing Figures

STEREOSELECTIVE INTRODUCTION OF TETRACYCLINES HYDROXYL GROUP AT 12(A) POSITION IN SYNTHESIS OF TETRACYCLINES

This is a continuation of application Ser. No. 832,680, filed June 17, 1969, now abandoned.

The present invention is concerned with a new method for the preparation of tetracycline compounds containing a 12a hydroxy substituent in the cis position relative to the 4a hydrogen atom. The stereoselective or stereospecific introduction of the 12a hydroxy group in the synthesis of tetracycline compounds is of considerable importance in the chemical synthesis of biologically active tetracycline-type antibiotics. However, the tetracycline compounds are useful for other purposes as well, most notably in those applications which take advantage of their effectiveness as chelating agents.

The basic nucleus of the 12a deoxy tetracyclines to which the present invention is applicable is the following

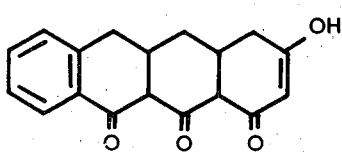

(1)

and

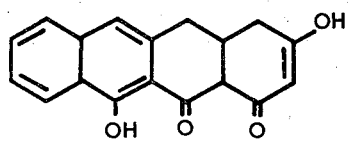

(1A)

These compounds exist in various tautomeric forms and, moreover, may be either mono or poly substituted in various positions such as the 2, 4, 5, 5a, 6, 7, 8, 9 and 10 positions. For example, typical substituents which may appear at these various positions include bromo, iodo, chloro, fluoro, trifluoromethyl, nitro, cyano, amino, cyanato, thiocyanato, azido, lower alkyl amino, hydroxy, alkanoyl amino, lower alkyl, and mono-substituted lower alkyl wherein the substituent may be fluoro, lower alkyl mercapto, lower alkoxy, amino, lower alkyl amino, alkanoyl oxy, and alkanoyl amino groups.

A wide variety of 12a deoxytetracyclines useful for the present purposes have been fully described in U.S. Pat. No. 3,188,348, the disclosure of which is hereby incorporated by reference.

Many of the 12a hydroxylation products which may be produced are of low biological activity or may be inactive. In some cases biologically active products may be obtained by the introduction of appropriate groups by chemical treatment or biochemical methods. However, as noted above, even those compounds having little or no value as biologically active agents can find application in other areas.

The readily available tetracyclines which are biologically active have the structure

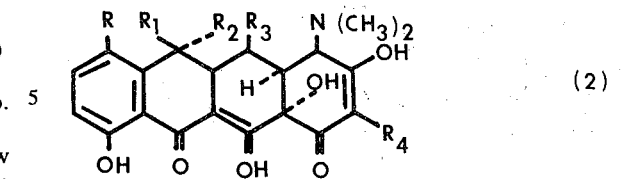

(2)

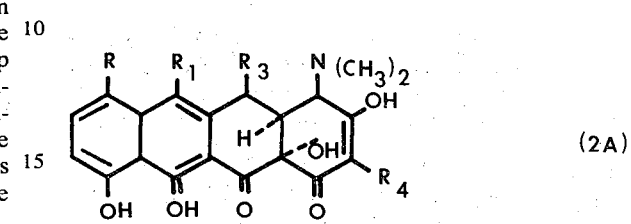

(2A)

wherein R is halide or hydrogen, $R_1$ is H or hydroxy, $R_2$ is hydrogen or methyl, $R_3$ is hydrogen or hydroxy, and $R_4$ is amido, alkyl amido, acetyl or cyano. The simplest member of the tetracycline family having full biological activity against both Gram-negative and Gram-positive bacteria is 6-deoxy-6-demethyltetracycline having the structure

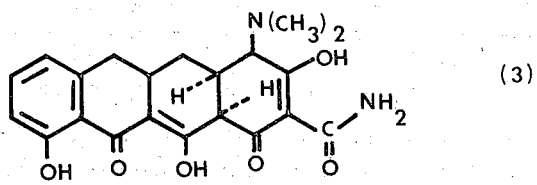

(3)

Other important members of the tetracycline family which have achieved wide commercial acceptance as antibiotics are the following:

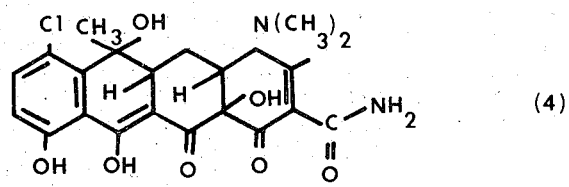

(4)

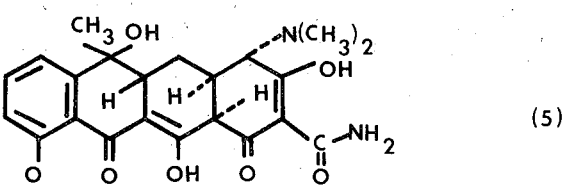

(5)

The chemical synthesis of tetracycline compounds has proved to be an extraordinarily difficult task. These difficulties are largely attributable to the chemical sensitivity of the tetracycline nucleus and to the fact that in its synthesis a number of asymmetric centers must be formed stereospecifically or stereoselectively.

Procedures which have been developed to date for the total synthesis of tetracyclic compounds have involved the preparation of a precursor having the nucleus:

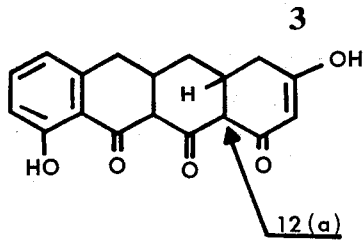

(1B)

which for brevity will be hereafter referred to in the specification and claims as "the tetracycline precursor." As noted above, tetracycline precursors useful in the present invention may contain a wide variety of substituent moieties on the basic ring structure set forth in formula (1B).

The present invention is concerned with a novel method for the stereospecific introduction of a 12a hydroxy group into the tetracycline precursor, as described in more detail below, which is predominantly cis or predominantly trans to the indicated hydrogen at the 4a position. It will be appreciated that the mirror-image isomers of compound (1B) may also be used with the 12a hydroxy group which is introduced, also assuming the mirror-image position.

BACKGROUND

By way of background, it is appropriate first to describe in summary a procedure which has been developed for the synthesis of an important tetracycline precursor from which oxytetracycline, having the structure of formula (5) above, may be readily obtained.

The procedure for the chemical synthesis of a tetracycline precursor from which oxytetracycline may be ultimately obtained is schematically set forth in the drawing.

It will be appreciated that the specific precursor — compound (20), shown in the drawings — is also accessible through microbial synthesis coupled with suitable chemical manipulation of the fermentation product. It is also pointed out that the present invention is concerned not only with the cis 12a hydroxylation of this specific precursor but also with the stereospecific or stereoselective hydroxylation of tetracycline precursors generally as defined in formulas 1B and 1D above, however these precursors may be prepared. A wide variety of precursors may be prepared, for example, following the basic procedure illustrated with specific reference to the preparation of oxytetracycline, making suitable substitutions and modification of reactants where other tetracycline compounds are desired.

The tetracycline precursor for the synthesis of oxytetracycline is assembled from three basic building blocks: The thiazolone of the structure,

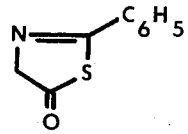

(6)

methyl 3-oxoglutaramate having the formula

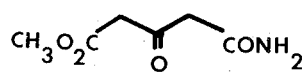

(7)

and the aldehyde having the formula

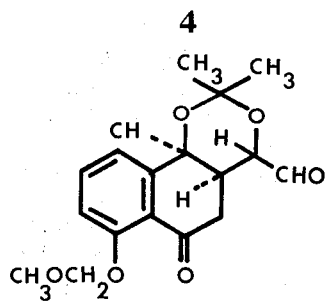

(8)

The thiazolone (6) is prepared by the treatment of thiobenzoglycine as described, for example, by Muxfeldt et al. in *Journal of the American Chemical Society*, Volume 89, pp. 4991–4996 (Sept. 13, 1967).

Methyl 3-oxoglutaramate, compound (7), is obtained by acid hydrolysis of the enamine $$CH_3O_2C-CH=C(NH_2)-CONH_2 \quad (9)$$

The enamine (9) is, in turn, prepared by a carefully controlled treatment of dimethyl-3-oxoglatarate with ammonia in methanol and is characterized by a melting point of 120°–121° C.

The aldehyde (8) is prepared starting with the addition of 1-acetoxybutadiene (11) to juglone acetate (10). [See drawing.] The tricyclic adduct (12) is converted to the aldehyde (13). A procedure for effecting this conversion is set forth in detail in the paper by Muxfeldt appearing in *Angewandte Chemie*, Volume 74, pp. 825–828 (1962). Briefly summarized, the procedure involves treating the adduct (12) in a Grignard reaction with methyl magnesium iodide which adds a methyl group to the 9a position.

(12a)

This intermediate is treated with absolute acetone and anhydrous copper sulfate to obtain the acetonide:

(12b)

Oxidation of the acetonide (12b) with potassium chlorate in the presence of a catalytic amount of osmium tetroxide resulted in the diol:

(12c)

Conversion of the diol (12c) to the aldehyde (13) was effected in a two-step reaction in which the diol was first oxidized with lead tetraacetate to form the dialdehyde (12d):

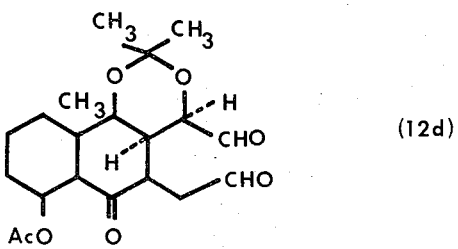

which, in turn, was cyclized to form the aldehyde (13).

Conversion of the aldehyde (13) to the mixed isomeric aldehydes (14) and (15) is performed by ozonolysis of aldehyde (13), water treatment of the resulting ozonide and cleavage of the reaction product with sodium carbonate. The pure isomers (14) and (15) were characterized by melting points of 140°–143° C and 171°–173° C, respectively.

Piperidine, in refluxing benzene, converted the aldehydes (14) and (15) to the enamine (16) in a 91 percent yield. Enamine (16) was characterized by a melting point of 118°–119° C. The enamine was alkylated with chloromethyl methyl ether to the methoxymethyl ether (17) (m.p. 81°–84° C). When (17) was adsorbed on deactivated silica gel, selective hydrolysis of the enamine function occurred, and the oily aldehyde (8) was formed in a 72 percent yield. The nuclear magnetic resonance spectrum was consistent only with a trans coplanar relationship of the hydrogens at the C-5 and C-5(a) positions, indicating that the hydrolysis through which the aldehyde (8) was formed was stereospecific.

Condensation of the aldehyde (8) with thiazolone (6) in the presence of basic lead acetate in tetrahydrofuran results in thiazolone (18) characterized by a melting point of 157°–160° C.

A combination of strong bases (for example, butyllithium and potassium t-butoxide) catalyzed the reaction of thiazolone (18) with methyl 3-oxoglutaramate (7) to yield the tetracyclic compound (19) characterized by a melting point of 225°C (with decomposition). In general, any strong base may be used which does not destroy the desired tetracyclic product. The reaction was carried out under reflux conditions with tetrahydrofuran as a solvent. The methoxymethyl group was then removed by acetic acid to obtain the tetracycline precursor (20).

The present invention is concerned with the treatment of tetracycline precursors of formula (1B) (compound (20) being a typical such precursor) under conditions resulting in the introduction of a hydroxyl group at the 12a position in a predominantly cis position relative to the 4a hydrogen. More specifically, in accordance with the present invention, introduction of this hydroxyl group is achieved by reacting compound (20) with molecular oxygen in a basic medium employing a non-protic solvent. For the best yields, a peroxide-destroying agent is also provided in the reaction system.

The solvent employed in the present invention is one which does not destroy the desired product in the presence of a strong base. In general these are nonprotic solvents, i.e., solvents which do not release protons in the presence of a strong base. Exemplary solvents include, but are not limited to benzene, toluene, xylene, diglyene, tetrahydrofuran, dioxane, diethyl ether, anisole (as well as a variety of other ethers), dimethyl formamide, dimethyl sulfoxide and ethyl acetate. Other solvents analogous to the foregoing will be obvious to those skilled in the art, including some of the solvents mentioned in the above-cited U.S. Pat. No. 3,188,348.

The strong base used in the present invention must be one having sufficient strength to ionize the hydroxy groups in the tetracycline structure, but, at the same time, be one which will not destroy the product. In general, bases such as the alkali metal amides, the alkali metal butoxides and alkyls of 1-6 carbons and hydrides. Sodium hydride, sodamide, lithium alkyl and potassium t-butoxide are typical. It will be apparent that some of these materials, for example potassium hydride, are hazardous to handle, and are preferably avoided where more convenient alternative materials are available. As a rule, the polyvalent alkoxides, hydrides, alkyls, and the like have been found to be unsuitable, although magnesium alkoxides can be used. The alkali metal hydroxides are also unsuitable because of their destructive effect on the tetracycline.

Finally, the presence of a peroxide-destroying agent is preferred since any peroxides formed during the oxygenation step will destroy the desired tetracyclic product and thereby reduce the yield. Suitable peroxide-destroying agents are trialkyl phosphites, palladium or platinum metal, alkali metal ascorbates, peroxidase enzymes, mercaptans, sulfides, sulfones, and various phosphines. The peroxide-destroying agent should be one which will not attack the tetracycline structure itself. Obviously, materials which are difficult to handle such as the mercaptans and sulfides are not preferred.

It has been found that a small amount of moisture is sometimes necessary to initiate the reaction. Where the reaction seems to start with difficulty, a few drops of water may be added to the reaction mixture.

Treatment of a tetracycline precursor, of which compound (20) is representative, under the foregoing conditions with dry molecular oxygen (either pure oxygen or air) for a period of 2 to 15 minutes. The temperature is typically about room temperature, although in principle any temperature between the freezing point and boiling point of the solvent may be used.

In the preferred practice of the present invention the time of the reaction is adjusted so that it is just sufficient to consume the starting material. This may be conveniently accomplished by following the course of the reaction photometrically or colorimetrically. This have been found to optimize the yield. Extended reaction beyond that just sufficient to consume the reaction product tends to cause degradation and loss of the desired product.

Acid treatment of the hydroxylated product removes the acetonide group bridging the C-5 and C-6 positions of the tetracycline ring structure. Conversion of tetracycline (21) into oxytetracycline (5) is then but a simple step involving removal of the thiobenzamide chromophore and substituting a dimethylamino group.

The present invention is more fully illustrated by reference to the following examples:

EXAMPLE 1

Examples 1 is devoted to setting forth a method for the preparation of a typical tetracycline precursor (specifically precursor (20)) as shown in the drawings.

1. (a) Oxidation of diol (12c)*

*This preparation is reported in the doctoral thesis of Edwin Vedejs submitted to the University of Wisconsin in 1966.

The diol (12c) (105 gms.) of the structure:

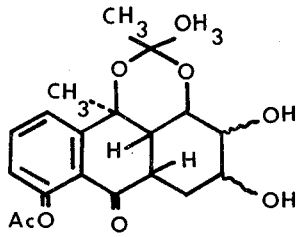

was dissolved in acetone (5 liters, technical grade, distilled twice from anhydrous potassium carbonate) at 40° C in a 12-liter, 3-neck flask equipped with a stirrer, condenser, and a drying tube. Lead tetraacetate (157.5 gms., dried 8 hours at 40° C under vacuum) was added at once and stirring was maintained for one hour at 40° C. The heating bath was removed and 5 liters of hexane were added. After 10 minutes the lead salts were filtered and washed thoroughly with 2 liters of a 1:1 benzene-chloroform mixture. The organic phase was combined, evaporated, and dissolved in chloroform. The chloroform solution was washed twice with water, dried over sodium sulfate, and evaporated to yield the dialdehyde (12d) as a yellow oil. The material was pure enough for use in the next step.

Dialdehyde (12d) was recrystallized from ether and characterized by a melting point of 135°–138° C. In addition, the structure assigned to it was verified by infrared, ultraviolet, and nuclear magnetic resonance spectra and by elemental analysis.

1. b. Cyclization to Unsaturated Aldehyde (12d)*

*This preparation is reported in the doctoral thesis of Edwin Vedejs submitted to the University of Wisconsin in 1966.

The oily dialdehyde (12d) prepared as described in Example 1(a) was dissolved in xylene (reagent grade, 2.1 liters) and separated into 7 aliquots of 300 milliliters. Each aliquot was placed into a 2-liter, 3-neck flask equipped with a condenser and a water separator. Xylene was added to bring the volume of each flask up to 750 milliliters and the mixture was brought to reflux. A solution of diazabicyclooctane (4.5 grams) in acetic acid (75 milliliters) was added at once while vigorous boiling was maintained and followed by the addition of a solution of 0.5 grams of piperidine in 25 milliliters of xylene. The dark red solution was then refluxed 7 minutes. Heating was stopped and chilled benzene (750 milliliters) was added, and the mixture was cooled for 2 minutes in an ice bath. The dark brown solution was rapidly washed 5 times with water (1 liter portions). The aqueous phase was reached with benzene (2 liters) and the combined organics were dried over sodium sulfate. The seven organic-phase products were combined and evaporated at 60° C on a flash evaporator. The last traces of xylene were removed under vacuum to yield a dark, partly crystalline gum. The product was heated with ether (250 milliliters) until all gummy material had dissolved, and allowed to crystallize at room temperature. The brown crystalline material was filtered and washed free of gum with cold ether containing 20% benzene to give 51 grams of the unsaturated aldehyde. It was characterized by a melting point of 162°–165° C (decomposition) after being recrystallized three times from ether. Its structure was verified by infrared, ultraviolet, and nuclear magnetic resonance sprectroscopy and by elemental analysis.

1. c. Ozonolysis of the Unsaturated Aldehyde (13)*

*This preparation is reported in the doctoral thesis of Edwin Vedejs submitted to the University of Wisconsin in 1966.

A solution containing 5 grams of the unsaturated aldehyde (13) in 300 milliliters of chloroform (distilled from phosphorus pentoxide) was chilled to −50° C. Ozone, 10% in excess of the stoichiometric amount, from a calibrated generator was passed through for 65 minutes between −40° and −50° C. Excess ozone was then removed by passing nitrogen through the cold solution. The mixture was allowed to come to room temperature and used directly in the next reaction. An analytical sample of the ozonide was obtained by removing solvent at 35° C and crystallizing several times from ether. A characteristic melting point of 104° (decomposition) was noted. The sample was further characterized by means of its infrared and ultraviolet spectra and by means of an elemental analysis.

Water (25 milliliters) was added to the chloroform solution of the ozonide directly after ozonolysis and the two-phase mixture was allowed to stand at room temperature for two days with occasional shaking. The aqueous phase was then separated and the chloroform layer dried over sodium sulfate, and evaporated at 40° C. The pale orange residue was taken up in ether containing a little chloroform (20 milliliters total) and the solution allowed to evaporate slowly at room temperature. Several crops of cream-colored crystals were collected over 2 days, with a total yield of 3.7 grams. The crystals were characterized by a melting point of 130° – 138° C (decomposition). However, because of the chemical instability of the crystals at room temperature, satisfactory analysis of them could not be obtained.

The orange crystals were dissolved in 1 liter of distilled methylene chloride. A solution of 0.5 N sodium carbonate (500 milliliters) was added, and the mixture was vigorously stirred for two hours. The red water layer was separated, washed with methylene chloride (200 milliliters) and discarded. The combined organic phases were washed with water (500 milliliters), dried over sodium sulfate, and evaporated. The residual oil crystallized from ether (200 milliliters) to yield a crystalline material characterized by a melting point of 120°–160° C. this crystalline material being a mixture of the isomeric aldehydes (14) and (15). The structure of the mixture of the aldehydes (14) and (15) was carefully verified by means of infrared, ultraviolet and nuclear magnetic resonance spectra of the separate aldehydes (14) and (15) and by elemental analysis.

1. (d) Preparation of Enamine (16)*

*This preparation is reported in the doctoral thesis of Edwin Vedejs submitted to the University of Wisconsin in 1966.

The mixture of aldehydes (14) and (15) as prepared in Example 1c was dissolved in benzene (125 milliliters, distilled from lithium aluminum hydride). Piperidine (2.8 grams distilled from potassium hydroxide) was added and the red solution was refluxed under a water separator for one hour. The solvents were then removed to obtain a brown, crystalline residue. The product, when recrystallized from ether, was characterized by a melting point of 114°–118° C. The identification of the product was confirmed using infrared, ultraviolet and nuclear magnetic resonance spectra and by elemental analysis.

1. (e) Etherization of Enamine (16)*

*This preparation is reported in the doctoral thesis of Edwin Vedejs submitted to the University of Wisconsin in 1966.

The enamine (16) was dissolved in dry tetrahydrofuran (250 milliliters refluxed 8 hours over potassium hydroxide and distilled from lithium aluminum hydride) under nitrogen and the system cooled to 0° C. Sodium hydride (washed free of mineral oil with dry hexane and weighed under nitrogen) was added and the mixture allowed to warm slightly to start salt formation. Foaming was controlled by cooling the reaction vessel with ice water. When no more bubbling was apparent (about 30 minutes were required), freshly distilled chloromethylmethyl ether was added dropwise over a period of 1.5 hours under nitrogen while stirring. After a total of 6 hours stirring at room temperature, the solvent was evaporated at 35° C. The yellow residue was taken up in ether and the precipitated sodium chloride filtered off. The ether was evaporated and the orange oil crystallized from hexane. The resulting crystalline product was recrystallized twice from ether-hexane and characterized by a melting point of 83°–85° C. The structure of the resulting enamine ether (17) was confirmed employing infrared, ultraviolet and nuclear magnetic resonance spectroscopy and by elemental analysis.

1. (f) Preparation of Aldehyde (8)*

*This preparation is reported in the doctoral thesis of Jared Ben Mooberry submitted to Cornell University in February 1969.

10 grams of the enamine (17) as prepared through Example 1(e) were dissolved in 500 milliliters of dry benzene. Silical gel (300 grams, 60–250 mesh) deactivated with 80 milliliters of water was added and the slurry was stirred for 3 hours at room temperature. The solvent was then filtered off using a 5-inch diameter Buchner funnel. 2 liters of ethyl acetate - ether (25:75) was used to wash the silica gel. Evaporation of the solvent (benzene filtrate plus wash solvents) yielded about 10 grams of the viscous, oily, aldehyde (8). The product was used without further purification.

1. (g) Preparation of Thiazolone (18)*

*This preparation is reported in the doctoral thesis of Jared Ben Mooberry submitted to Cornell University in February 1969.

A solution of the simple thiazolone (6) was prepared by combining dicyclohexylcarbodiimide (5.19 grams) and thiohippuric acid (4.90 grams) in 150 milliliters of tetrahydrofuran and stirring for one hour at room temperature. The aldehyde (8) prepared in Example 1(f) was dissolved in 100 milliliters of tetrahydrofuran, and basic lead acetate (3.8 grams, lead analysis 33% PbO) was added to the solution. The slurry of simple crude thiazolone and dicyclohexylurea was added in two equal portions to the vigorously stirred solution of aldehyde (8) and lead acetate. The second portion of the simple thiazolone slurry was added thirty minutes after commencing the reaction which proceeded for a total of 1 hour at room temperature. The heterogeneous mixture was filtered through a sintered glass finnel using celite to prevent clogging of the funnel pores. The filtrate was evaporated under reduced pressure, dissolved in 50 milliliters of chloroform, and slurried with 40 grams of silica gel. The slurry was filtered using a large sintered glass funnel and washed with chloroform and ether. The combined filtrate was concentrated and crystallized from ether. Identification of the product thus obtained was verified by comparing its nuclear magnetic resonance spectrum with the spectrum of a like preparation whose authenticity had previously been confirmed by nuclear magnetic resonance, infrared, and ultraviolet spectroscopy and by elemental analysis.

The procedure described in Example 1(g) may also be carried out using the phosphorous tribromide method for the preparing of the simple thiazolone (6) which is described by Muxfeldt et al. in the *Journal of the American Chemical Society*, Volume 89, page 4991.

1. (h) Preparation of Methyl-3-Oxoglutaramate (7)*

*This preparation is reported in the doctoral thesis of Jared Ben Mooberry submitted to Cornell University in February 1969.

Hydrolysis of 22 grams of the recrystallized enamine (9) having the formula

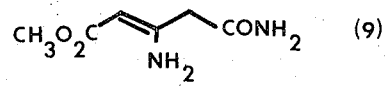

(in 360 milliliters of chloroform) proceeded rapidly on the addition of 12 milliliters of concentrated hydrochloric acid with vigorous stirring. 20 grams of anhydrous magnesium sulfate were then added after hydrolysis was complete. The solution was filtered and concentrated under vacuum. Crystallization from ethyl acetate yielded 13.2 grams of a white crystalline material characterized by a melting point of 36°–38° C. The identity of the product thus obtained was verified by infrared, ultraviolet and nuclear magnetic resonance spectroscopy and by elemental analysis.

1. (j) Thiazolone Condensation to Tetracyclic Substance (19)*

*This preparation is reported in the doctoral thesis of Jared Ben Mooberry submitted to Cornell University in February 1969.

The 500 milliliter round bottom flask and all other apparatus used in this example were oven dried at 125° C. All reactions were carried out under nitrogen atmosphere (except for work-up). Tetrahydrofuran was distilled from lithium aluminum hydride and stored under nitrogen until use.

Methyl-3-oxoglutaramate (7) prepared through Example 1(h) (3.18 grams) was dissolved in 85 milliliters of tetrahydrofuran in the reaction vessel. After cooling the solution to −78° C, butyl lithium (7.7 milliliters of a 2.6 molar solution in hexane) was added. The homogeneous solution was stirred for 10 minutes while a solution of thiazolone (18) prepared through Example 1g (9.5 grams) in 180 milliliters of tetrahydrofuran was prepared. The thiazolone solution was added slowly to the vigorously stirred solution of the half-amide salt while maintaining the temperature at −78° C. This mixture was warmed to room temperature over 1½ hours before refluxing for an additional 1½ hours. After cooling to −78° C again the homogeneous mixture was treated with 1 milliliter of tertiary butanol (decanted from calcium hydride) and 3.8 milliliters of butyl lithium. The mixture was warmed to room temperature over about 20 minutes, and 270 milligrams of potassium tertiary butoxide was added. The mixture was heated at 50° C for 1 hour then refluxed for 2 hours. Further quantities of potassium tertiary butoxide were added 50 minutes after refluxing had started (0.38 grams) and again 95 minutes after reflux had started (1.0 grams). The hot solution, following refluxing, was allowed to cool to room temperature for one hour and then neutralized with 6 milliliters of acetic acid.

After neutralization, the reaction mixture was concentrated under reduced pressure, dissolved in chloroform, washed with water, evaporated several times from a mixture of benzene, ethanol and chloroform to remove the last traces of water, and then dissolved in chloroform-ether. Crystallization of the product from the chloroform-ether solution was initiated by the addition of silica gel. The precipitated product and silica gel were removed by filtration and washed with chloroform and ether. The combined filtrates were concentrated, dissolved in a small amount of chloroform, seeded with a little product and allowed to crystallize again. 2.5 grams of the tetracycline (19) were obtained. It was characterized, upon recrystallization from acetone, by a melting point of 225° C (decomposition). The structure of the isolated product (19) was verified mainly by its ultraviolet spectrum and the fact that upon hydrolysis it was converted to the tetracycline (20). The structure of the product was further confirmed by infrared and nuclear magnetic spectroscopy and by elemental analysis.

1. (k) Preparation of Tetracycline Precursor (20)*

*This preparation is reported in a doctoral thesis of Jared Ben Mooberry submitted to Cornell University in February 1969.

The cyclization product (19) prepared in Example 1(j) (2.4 grams) was added to a 500 milliliter roundbottom flask containing 200 milliliters of acetic acid and 200 milliliters of water. This mixture was stirred and heated rapidly over a 6-minute period to reflux temperature at which time the solution had become homogeneous. After refluxing for 2 minutes, the solution was cooled rapidly in cold water, then concentrated under reduced pressure. The temperature did not exceed 30° C during evaporation. Crystallization from chloroform yielded 2.0 grams of precursor (20) which was characterized by a melting point of 220° C (with decomposition). Thin layer chromatography on a polyamide (carbon tetrachloride : benzene : formic acid, 100:100:1) showed no evidence of epimerization at the C-4 position during hydrolysis. The structure of tetracycline precursor (20) was confirmed by infrared, ultraviolet and nuclear magnetic resonance spectroscopy and by elemental analysis.

EXAMPLE 2

Cis 12(a) Hydroxylation of Tetracycline Precursor (20)*

*This preparation is reported in a doctoral thesis of Jared Ben Mooberry submitted to Cornell University in February 1969.

The tetracycline precursor (20) (524 milligrams) was dissolved in 50 milliliters of tetrahydrofuran and 50 milliliters of dimethylformamide (decanted from calcium hydride). Triethyl phosphite (0.25 milliliters distilled from sodium) and sodium hydride (60% dispersion in oil, 350 milligrams) were then added to the solution. Oxygen was bubbled through the solution via a gas dispersion tub for 15 minutes. Water (0.14 milliliters) was added slowly during the first 3 minutes. The reaction appeared to be over after 10 minutes since an aliquot in borate solution had very little absorption at 450 millimicrons. Acetic acid and water were added (vigorous hydrogen evolution) until a homogeneous solution was obtained and a pH of about 5 was reached.

A total of 300 milliliters of water was added before extraction with ethyl acetate. The organic extracts were washed several times with water to insure complete removal of dimethylformamide. After evaporating the ethyl acetate, the residue was dissolved in 20 milliliters of methanolic 0.01 N hydrochloric acid. Hydrolysis was allowed to proceed for 1½ hours at room temperature before extraction of the methanolic solution with hexane to remove mineral oil. The mixture was concentrated under vacuum, dissolved in ethyl acetate, washed with water to remove residual acid, and concentrated again. This concentrate was dissolved in 2 milliliters of methylene chloride containing 3 drops of formic acid and slurried with 2 grams of column grade polyamide powder. Air drying produced a freely-flowing powder which was applied to the top of a column containing 10 grams of polyamide pretreated with 2 milliliters of methylene chloride and 0.03 milliliters of formic acid. Methylene chloride was used to elute a yellow band consisting of a small amount of unreacted tetracycline precursor (20) and a second material which was presumed to be an 11(a)-hydroxylated by-product containing the acetonide linkage intact. The desired product was then eluted with acetone. Crystallization of the product from ethyl acetate gave 189 grams of a light yellow crystalline material characterized by a melting point of 200° C (decomposition). Identification of the product was confirmed by infrared, ultraviolet and nuclear magnetic resonance spectroscopy and by elemental analysis. The nuclear magnetic resonance spectrum clearly indicated the presence of one mole of ethyl acetate and the absence of the acetonide grouping.

EXAMPLE 3

Preparation of Oxytetracycline*

*This preparation is reported in a doctoral thesis of Jared Ben Mooberry submitted to Cornell University in February 1969.

The hydroxylated tetracycline (21) (206 milligrams) was allowed to stand with methyl iodide in 3 milliliters of tetrahydrofuran at room temperature for 20 hours. After another 12 hours at −20° C, the solvent was removed under vacuum. The concentrate was dissolved in 4 milliliters of tetrahydrofuran and 2 milliliters of 0.5 N hydrochloric acid. Hydrolysis proceeded for 1½ hours at room temperature. The mixture was diluted with water and extracted successively with ether, ethyl acetate, and n-butanol. The n-butanol extract was evaporated at 25° C under high vacuum to crystallize the amine hydrochloride of dedimethylaminoxytetracycline.

The amine hydrochloride (166 milligrams) was combined with N,N-diisopropylethylamine (0.122 milliliters), dimethyl sulfate (0.18 milliliters), 5 milliliters of tetrahydrofuran, and 0.04 milliliters of ethanol. The heterogeneous mixture was stirred magnetically for 17 hours at room temperature, and was still heterogeneous at the end of this time. This layer chromatography using a polyamide showed the major product at this time to be identical to authentic oxytetracycline. A small amount of methanol was added to the mixture to dissolve the solid and the solution was concentrated under vacuum to a viscous oil. One milliliter of tetrahydrofuran was added and the solution kept at −78° C for 24 hours. The solid which precipitated was removed by filtration. The filtrate was concentrated under vacuum and combined with 0.6 milliliters of N,N-diisopropylethyl amine, 2 drops of acetic acid, 1 milliliter of methylene chloride, and 1 milliliter of tetrahydrofuran. The solution was slurried with 1 gram of column grade polyamide and air dried to a free-flowing powder (about ½ hour exposure to air). Five grams of polyamide were pretreated with 5 drops of acetic acid and 5 drops of methylene chloride before being tamped tightly into a small column. The mixture of crude dl-oxytetracycline and polyamide was placed on top of the column, tamped firm and covered with a layer of sand. A yellow forerun was eluted with methylene chloride which left the dl-oxytetracycline adsorbed near the top of the column appearing as a reddish, fluorescent zone under 366 millimicrons illumination. The synthetic oxotetracycline was then eluted with acetic acid : acetone : chloroform (1:15:84). After evaporation to an amorphous solid, the racemic oxytetracycline was recrystallized from acetone. Infrared, ultraviolet and nuclear magnetic resonance spectroscopy and elemental analysis showed that the product was identical to that of authentic oxytetracycline and contained 0.8 miles of acetone (per mole of product) in the dry crystalline material. A biological asray of the product showed that the synthetic dl-oxytetracycline was almost exactly 50% as active as the authentic product prepared through fermentation.

Examples 1–3 are schematically represented by the sequence of structural formulas set forth on pages 29a, 29b and 29c.

EXAMPLE 4

1.0 grams of the tetracycline precursor having the structure:

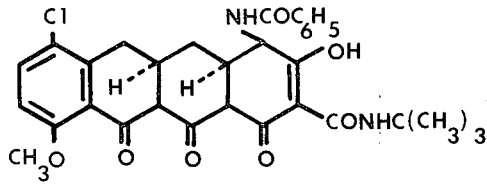

was dissolved in 40 milliliters of dimethyl formamide and 100 milliliters of tetrahydrofuran. Triethyl phosphite (280 milligrams) were added followed by 200 milligrams of sodium hydride dispersed in mineral oil. Oxygen was bubbled into the solution for 10 minutes and the color changed from a fluorescent orange to a dull green. A drop of this solution placed in methanolic sodium borate showed that the absorption in the visible region of the spectrum had disappeared and had been replaced by a new maximum at about 350 millimicrons. The oxygenated solution was then acidified with acetic acid, diluted with chloroform, washed 4 times with water, dried over sodium sulfate and evaporated. A cis hydroxylated tetracycline was obtained having the structure:

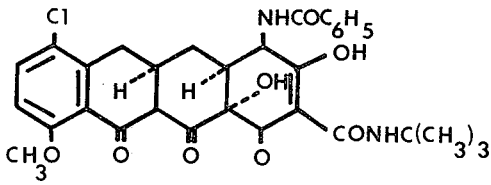

The structure of the resulting product was verified by infrared and ultraviolet spectroscopy and by elemental analysis. By-product materials were also recovered, there being 220 milligrams of a recrystallized material identified as having the hydroxy group in the trans position at the C-12 carbon atoms and 104 milligrams of a by-product identified as having the hydroxy group at the 11(a) position.

EXAMPLE 5

1.0 grams of the tetracycline precursor

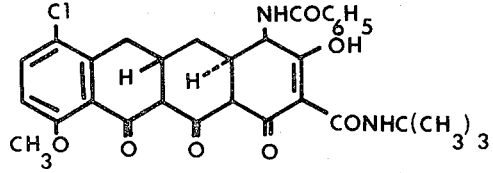

was hydroxylated with oxygen exactly as described in Example 4. In this case, however, the reaction was clean enough that after work-up, the product, which was assigned the structure

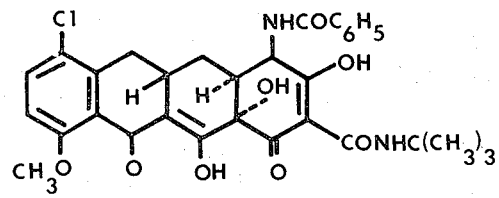

could be crystallized directly from methanol, 0.74 grams of the pure crystalline product was obtained. The structure assigned was verified by ultraviolet spectral analysis and elemental analysis.

Results similar to those set forth in Examples 2, 4 and 5 are expected where solvents such as diethyl ether, dioxane, anisole, toluene and benzene are substituted for the tetrahydrofuran - dimethyl formamide used in the above examples. Similarly, material such as dimethyl sulfoxide, triphenyl phosphine, and triethyl phosphine may be substituted for the triphenyl phosphite. Suitable strong bases which may be used in lieu of sodium hydride include potassium t-butoxide, buthyl lithium, phenyl lithium and sodamide.

EXAMPLE 6

0.500 grams of tetracycline precursor having the structure

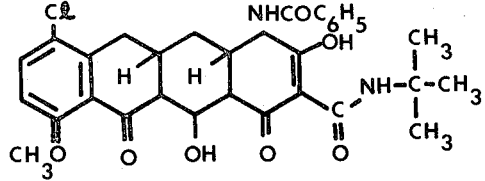

was hydroxylated exactly as described in Example 4. Upon chromatographic separation of the final product, two compounds were obtained:
  200 milligrams (40% yield of material hydroxylated trans at the C-12a position. The melting point was 275°–280° C with decomposition. The identity of the product was confirmed by spectrographic and elemental analysis; and
  50 milligrams (10% yield) of material hydroxylated cis at the C–12a position. The identity of the product was confirmed by spectrographic and elemental analysis.

We claim:

1. In the process for the stereospecific 12a hydroxylation of a 12a deoxytetracycline precursor wherein said precursor is contacted with molecular oxygen, said precursor being selected from the group consisting of

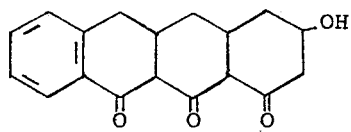

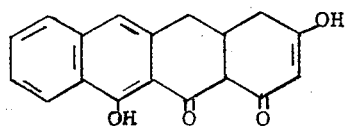

tautomeric forms thereof, and mono- or polysubstituted derivatives thereof having substituents selected from the group consisting of bromo, iodo, chloro, fluoro, trifluoromethyl, nitro, cyano, amino, cyanoto, thiocyanato, azido, lower alkyl amino, hydroxy, alkanoyl amino, lower alkyl, and lower mono-substituted alkyl having fluoro, lower alkyl mercapto, lower alkoxy, lower alkyl amino, alkanoyl oxy, and alkanoyl amino groups;

the improvement comprising carrying out said 12(a) hydroxylation in the presence of a strong base selected from the group consisting of alkali metal amides, alkali metal butoxides, alkali metal alkyls of 1 to 6 carbon atoms, alkali metal hydrides and magnesium alkoxides;

said reaction being carried out in the presence of a non-protic solvent which is inert with respect to the tetracycline structure in the presence of said strong base, and which does not release protons in the presence of said strong base.

2. A process according to claim 1 wherein said non-protic solvent is selected from the group consisting of tetrahydrofuran, dimethyl formamide, benzene, toulene, xylene, diglyene, dioxane, diethyl ether, anisole, dimethylsulfoxide and ethylacetate.

3. A process according to claim 1 wherein said peroxide-destroying agent is selected from a group consisting of trimethyl phosphite, palladium, platinum, alkali metal ascorbates, peroxidase enzymes, triphenyl phosphine and triethyl phosphine.

4. A process according to claim 1 wherein a small amount of water effective to initiate the hydroxylation reaction is added to the reaction solvent.

5. A process according to claim 1 wherein said 12(a) deoxytetracycline precursor is d,1-4-thiobenzamido-12(a)-deoxytetracycline.

6. A process according to claim 1 wherein said tetracycline precursor is d,1-2(N-t. butyl-amido)4-benzamido-6-deoxy-6-demethyl-7-chloro-10-methoxy12-(a)-deoxytetracycline.

7. A process according to claim 1 wherein said solvent is selected from the group consisting of dimethyl formamide and tetrahydrofuran.

8. A process according to claim 1 wherein said base is selected from the group consisting of sodamide, sodium hydride and potassium t. butoxide.

9. A process according to claim 1 wherein said peroxide-destroying agent is trimethyl phosphite.

* * * * *

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

First page, line 2 of Item [54], delete "TETRACYCLINES" (first occurrence);

First page, Item [63], "June 17" should read -- June 12 --;

First page, last line of Column 2, delete "3 Drawing Figures";

Column 1, line 2, delete "TETRACYCLINES"(first occurrence);

Column 1, line 6, "June 17" should read -- June 12 --;

Column 1, line 9, "12a" should read -- 12(a) --;

Column 1, line 10, "4a" should read --4(a) --;

Column 1, line 11, "12a" should read -- 12(a) --;

Column 1, line 18, "12a" should read -- 12(a) --;

Column 1, line 35, "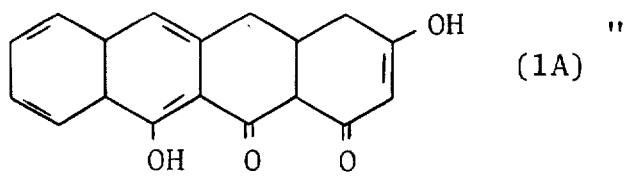"

should read

-- 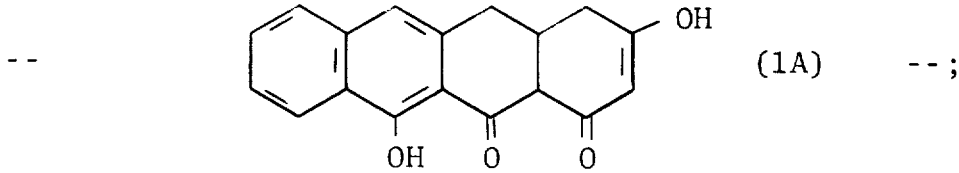 --;

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

Column 1, line 46, "5a" should read -- 5(a) --;

Column 1, line 56, "12a" should read -- 12(a) --;

Column 1, line 60, "12a" should read -- 12(a) --;

Column 2, line 15, "
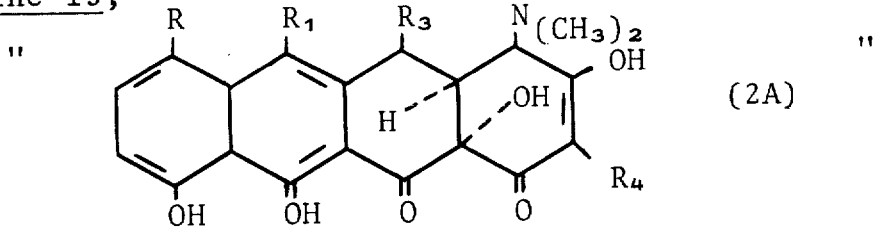
(2A)
"

should read

--
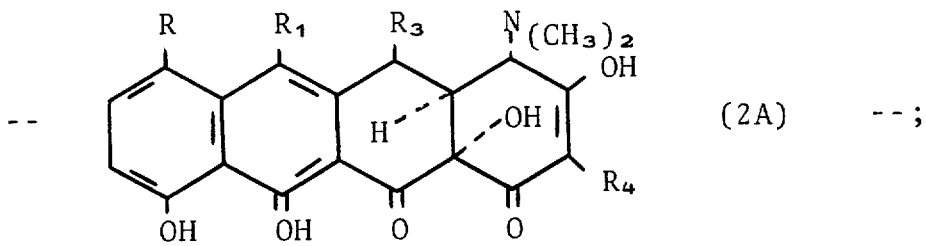
(2A)
--;

UNITED STATES PATENT AND TRADEMARK OFFICE
CERTIFICATE OF CORRECTION

PATENT NO. : 3,947,517  
DATED : March 30, 1976  
INVENTOR(S) : Muxfeldt et al.

Page 3 of 16

It is certified that error appears in the above-identified patent and that said Letters Patent are hereby corrected as shown below:

Column 2, line 30,

" 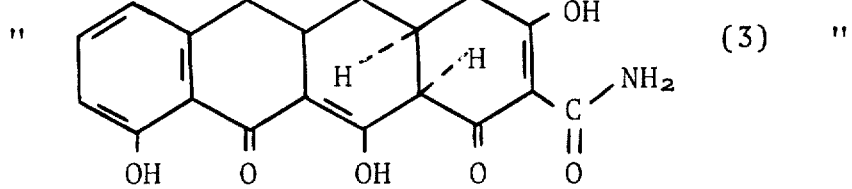 (3) "

should read

-- 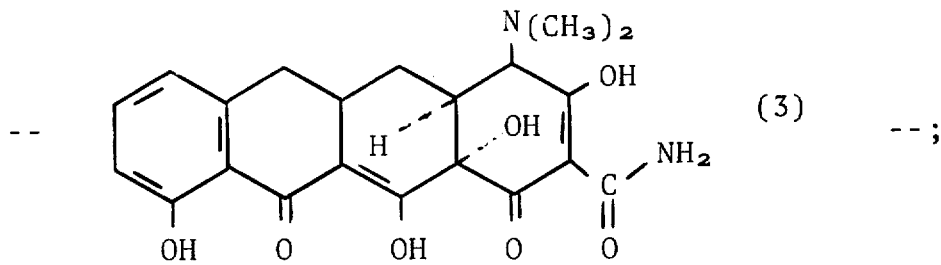 (3) --;

Column 2, line 45,

" 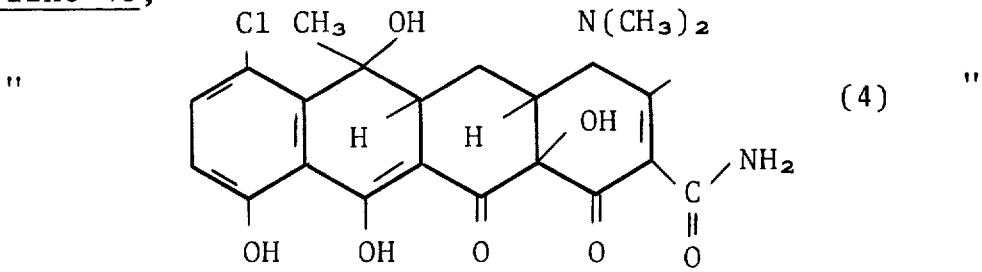 (4) "

should read

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

Page 4 of 16

It is certified that error appears in the above-identified patent and that said Letters Patent are hereby corrected as shown below:

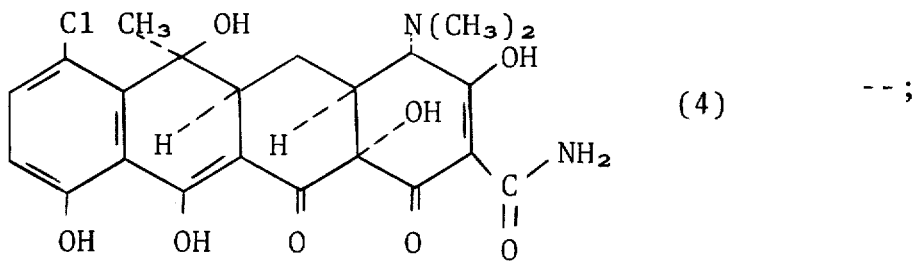 (4) --;

Column 2, line 55,

" 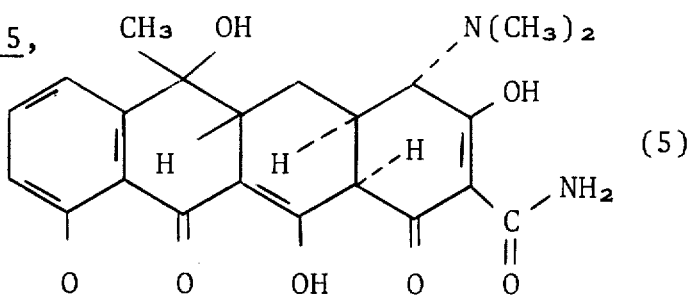 (5) "

should read

-- 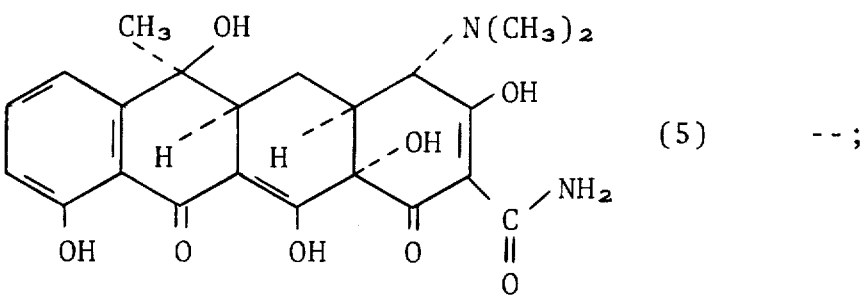 (5) --;

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

Column 2, line 67, "tetracyclic" should read -- tetracycline --;

Column 3, line 17, "12a" should read -- 12(a) --;

Column 3, line 21, "4a" should read -- 4(a) --;

Column 3, line 23, "12a" should read -- 12(a) --;

Column 3, line 42, "12a" should read -- 12(a) --;

Column 3, line 45, "formulas 1B and 1D" should read -- formula (1B) --;

Column 4, line 4, "CH" should read -- $CH_3$ --;

Column 4, line 24, "oxoglatarate" should read -- oxoglutarate --;

Column 4, line 36, "9a" should read -- 9(a) --;

Column 4, line 40, that portion of the formula reading

" 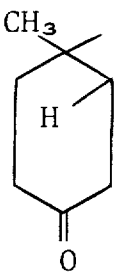 "  should read -- 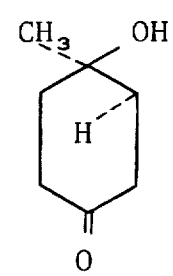 --;

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

Page 6 of 16

It is certified that error appears in the above-identified patent and that said Letters Patent are hereby corrected as shown below:

Column 4, line 50, that portion of the formula reading

Column 4, line 60,

"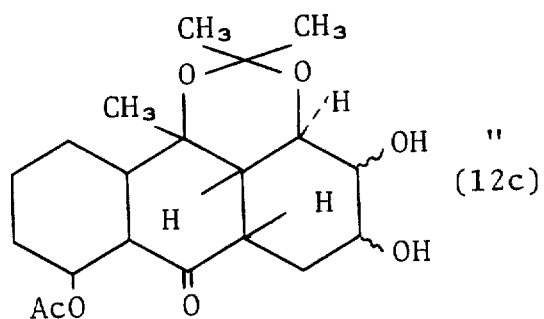

should read

--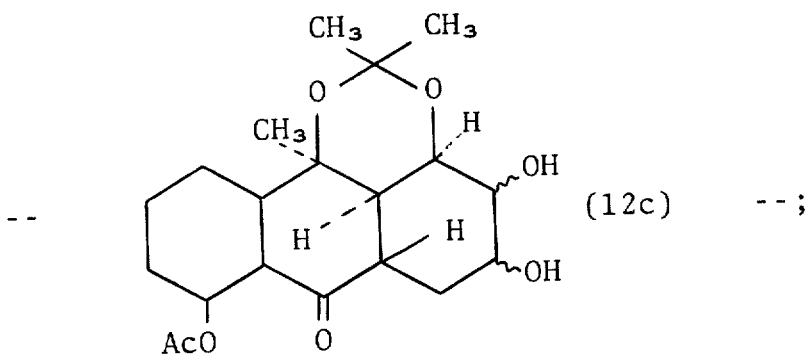--;

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

Column 5, between lines 49 and 50, insert -- The Invention --;

Column 5, line 55, "4a" should read -- 4(a) --;

Column 6, line 66, "Examples" should read -- Example --;

Column 7, line 10, " 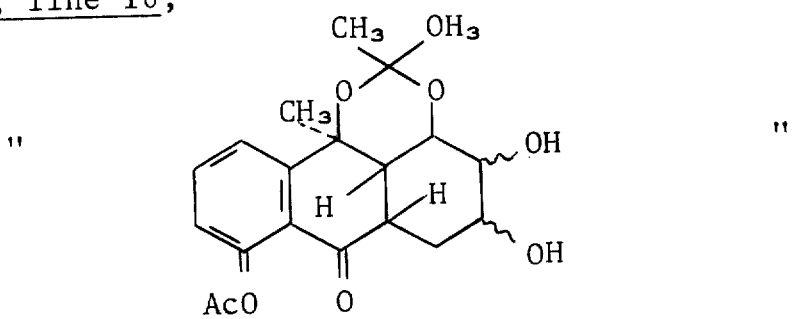 "

should read

-- 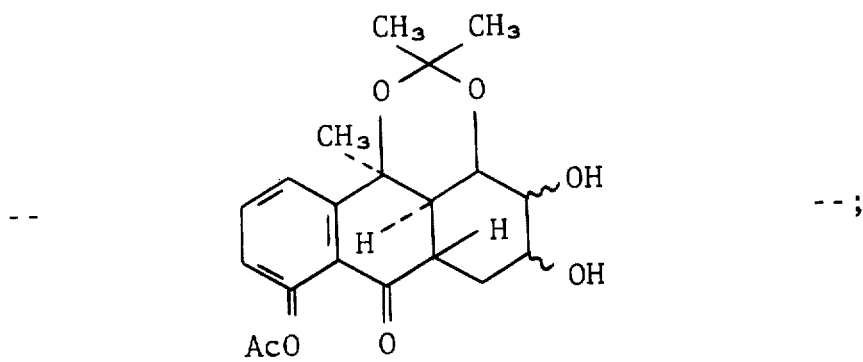 --;

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

Column 7, line 36, "b." should read -- (b) --;

Column 7, line 56, "reached" should read -- washed --;

Column 8, line 5, "c." should read -- (c) --;

Column 8, line 60, "1c" should read -- 1(c) --;

Column 9, line 64, "celite" should read -- Celite --;

Column 10, line 53, "1g" should read -- 1(g) --;

Column 10, line 61, "3.8" should read -- 8.8 --;

Column 11, line 59, "60%" should read -- 50% --;

Column 13, line 12, "dl-" should read -- d,1- --;

Column 13, line 23, "asray" should read -- assay --;

UNITED STATES PATENT AND TRADEMARK OFFICE
CERTIFICATE OF CORRECTION

PATENT NO. : 3,947,517

DATED : March 30, 1976

INVENTOR(S) : Muxfeldt et al.

It is certified that error appears in the above-identified patent and that said Letters Patent are hereby corrected as shown below:

-- 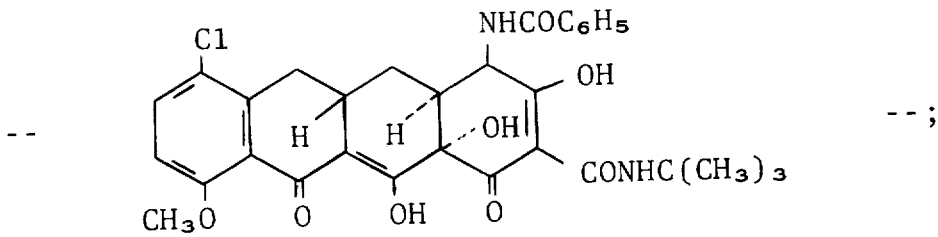 --;

Column 14, line 29, change the comma to a period;

Column 14, line 50,

" 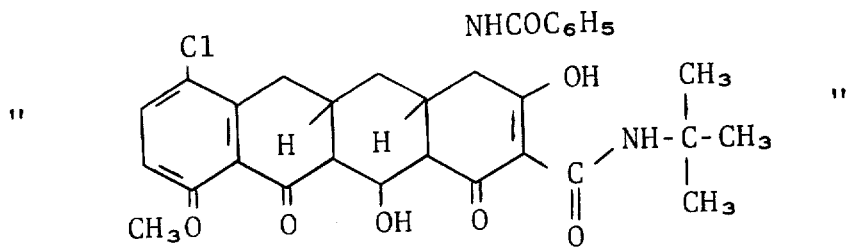 "

should read

-- 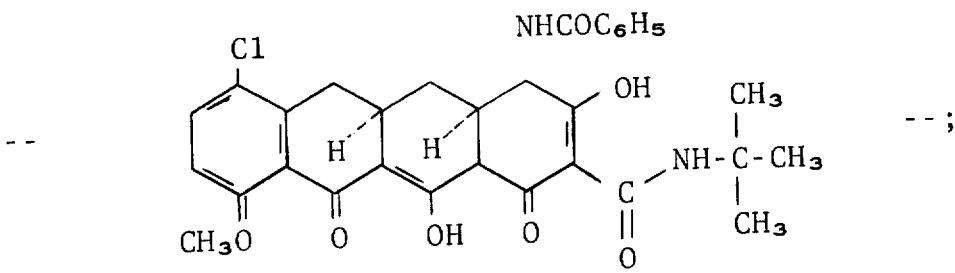 --;

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

Column 15, line 1, "12a" should read -- 12(a) --; and

Column 15, line 2, "12a" should read -- 12(a) --.

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

Column 14, line 68, insert the following:

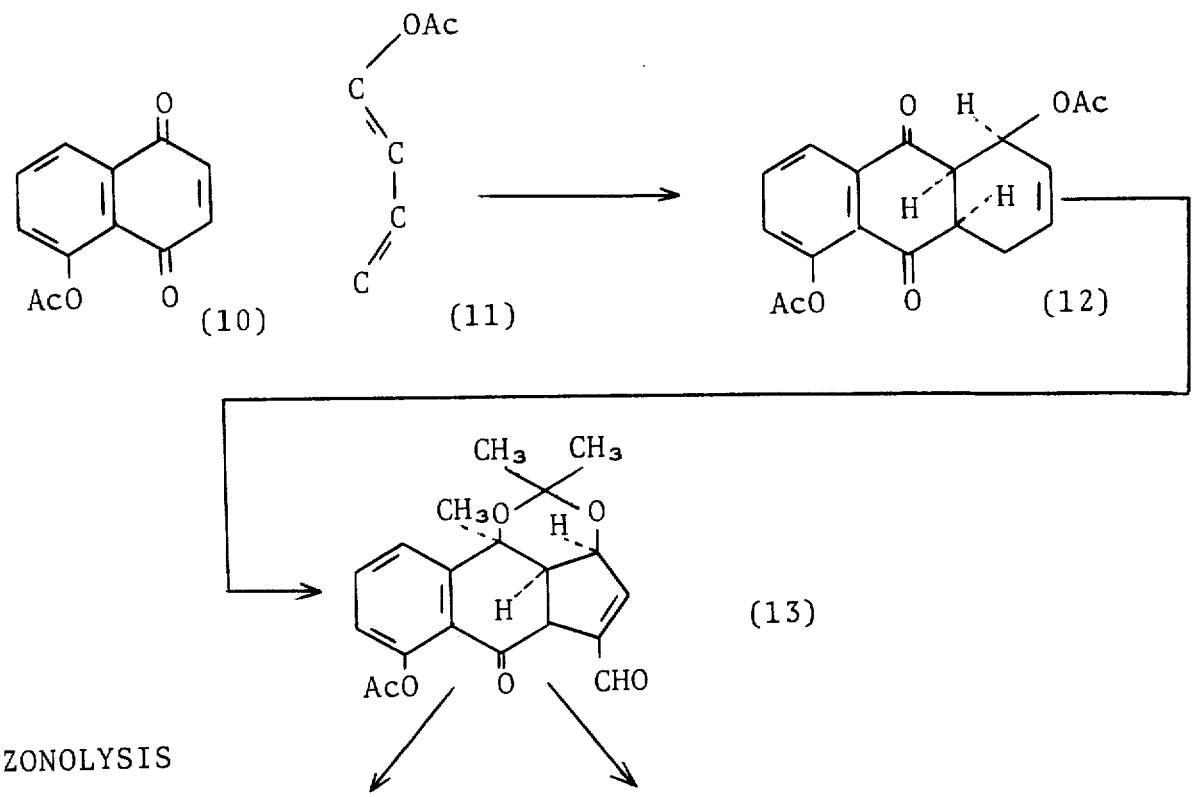

OZONOLYSIS

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

Page 12 of 16

It is certified that error appears in the above-identified patent and that said Letters Patent are hereby corrected as shown below:

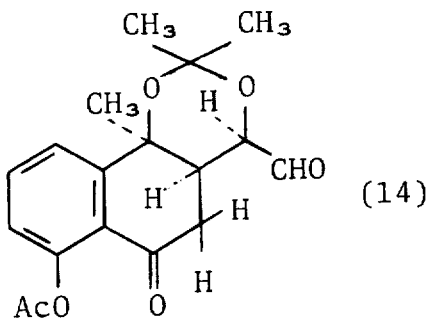 (14)

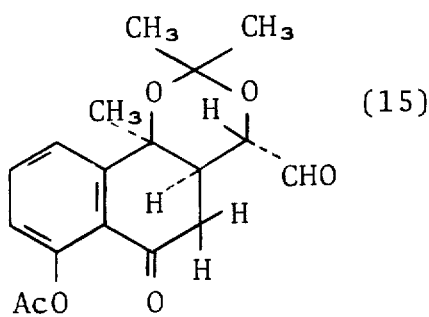 (15)

+PIPERIDINE

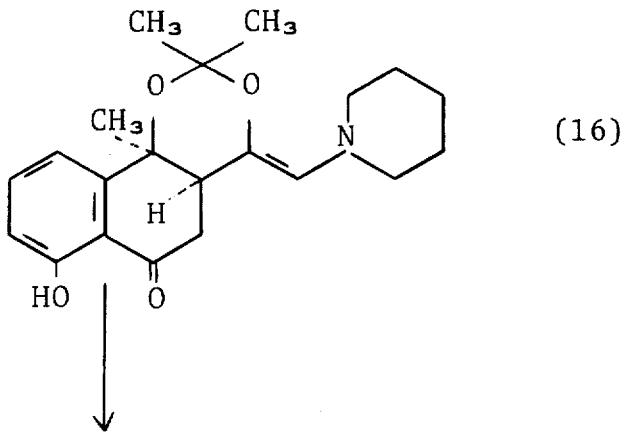 (16)

ETHERIZATION

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

Page 13 of 16

It is certified that error appears in the above-identified patent and that said Letters Patent are hereby corrected as shown below:

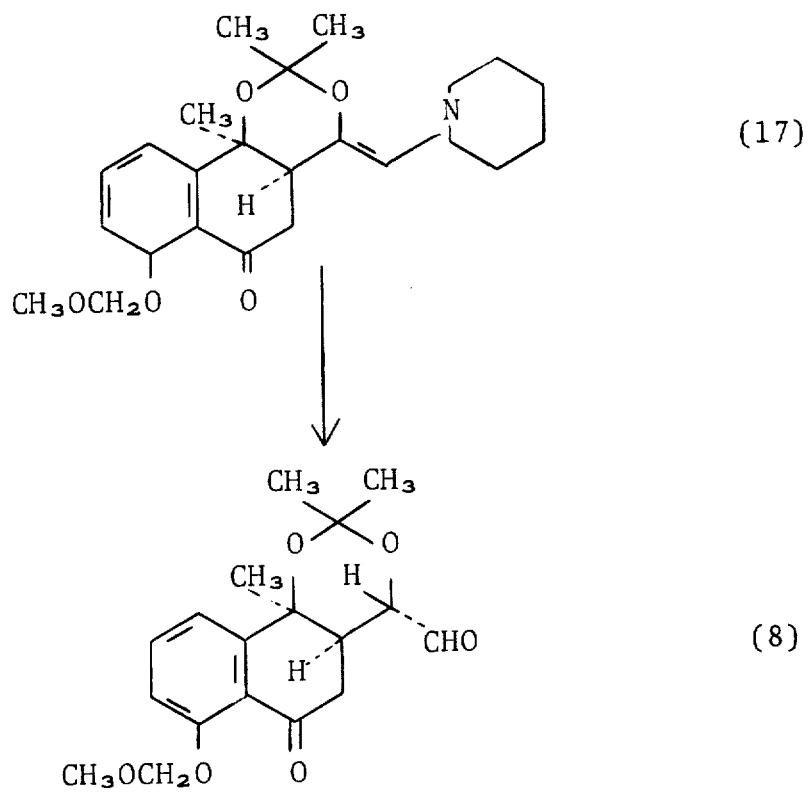

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

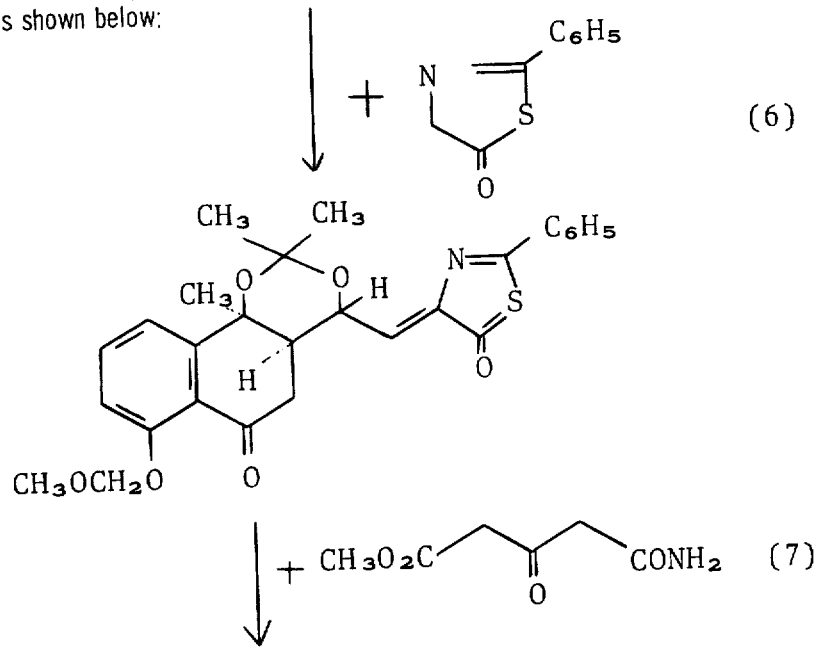

(6)

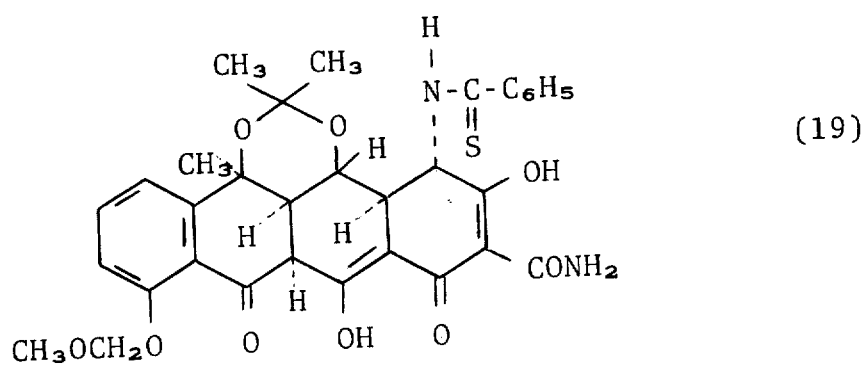

(7)

(19)

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

Page 15 of 16

It is certified that error appears in the above-identified patent and that said Letters Patent are hereby corrected as shown below:

REMOVE METHOXYMETHYL ETHER

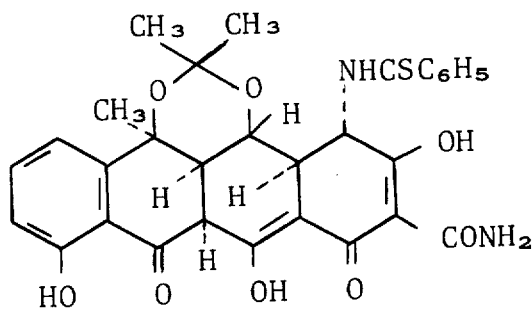

(20)

HYDROXYLATION
(KEY STEP)

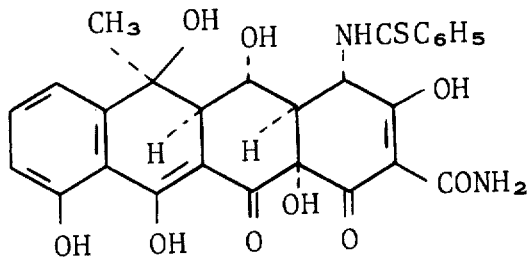

(21)

UNITED STATES PATENT AND TRADEMARK OFFICE
CERTIFICATE OF CORRECTION

PATENT NO. : 3,947,517
DATED : March 30, 1976
INVENTOR(S) : Muxfeldt et al.

It is certified that error appears in the above-identified patent and that said Letters Patent are hereby corrected as shown below:

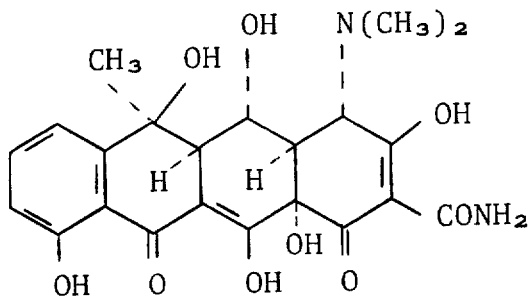

(5)

Signed and Sealed this

Fifth Day of October 1976

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

Column 3, line 45, "formulas 1B and 1D" should read -- formula (1B) --;

Column 4, line 24, "oxoglatarate" should read -- oxoglutarate --;

Column 13, line 28, delete "on pages 29a," and substitute therefor -- at Column 14, line 68 through Column (appropriate number), line (appropriate number). --;

Column 13, line 29, delete "29b and 29c.";

Column 14, after line 67 insert the following formulas.

Page 2 of 8

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

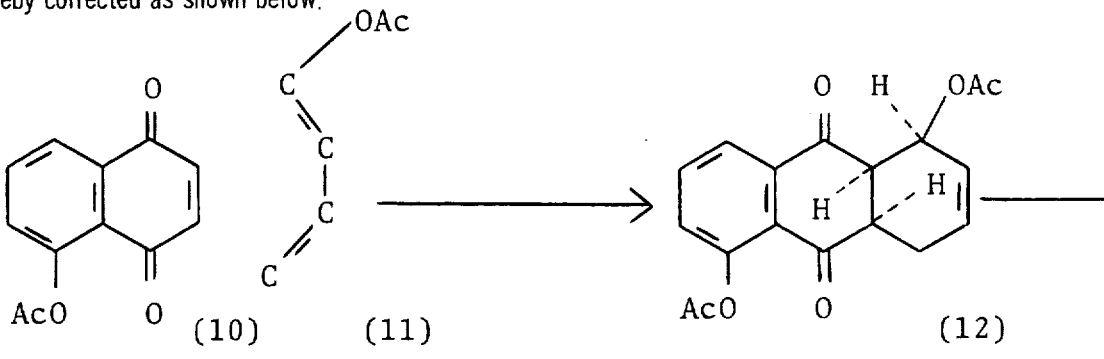

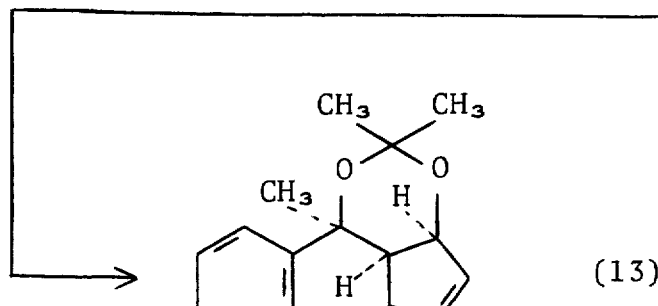

OZONOLYSIS

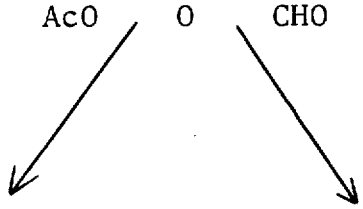

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

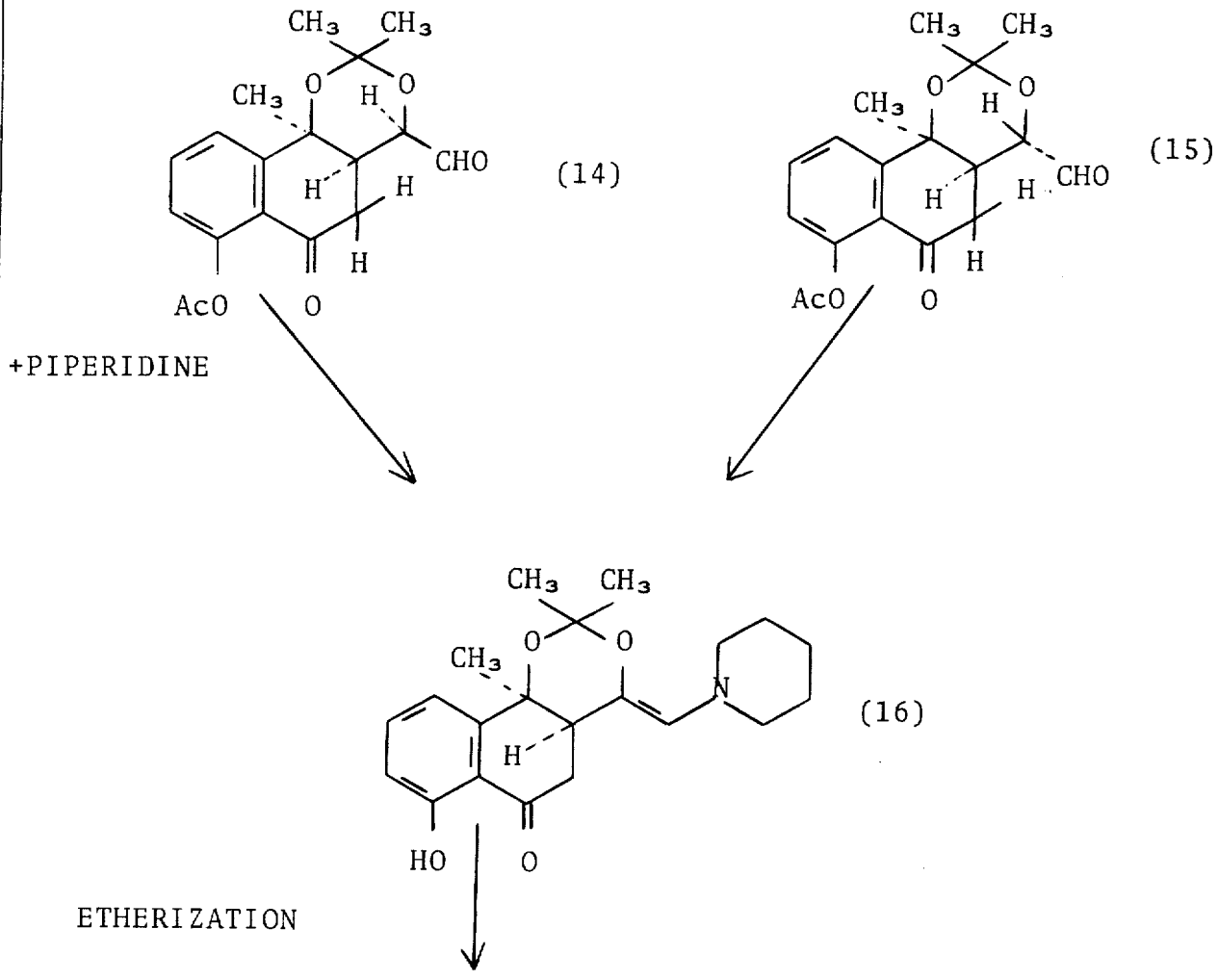

+PIPERIDINE

ETHERIZATION

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

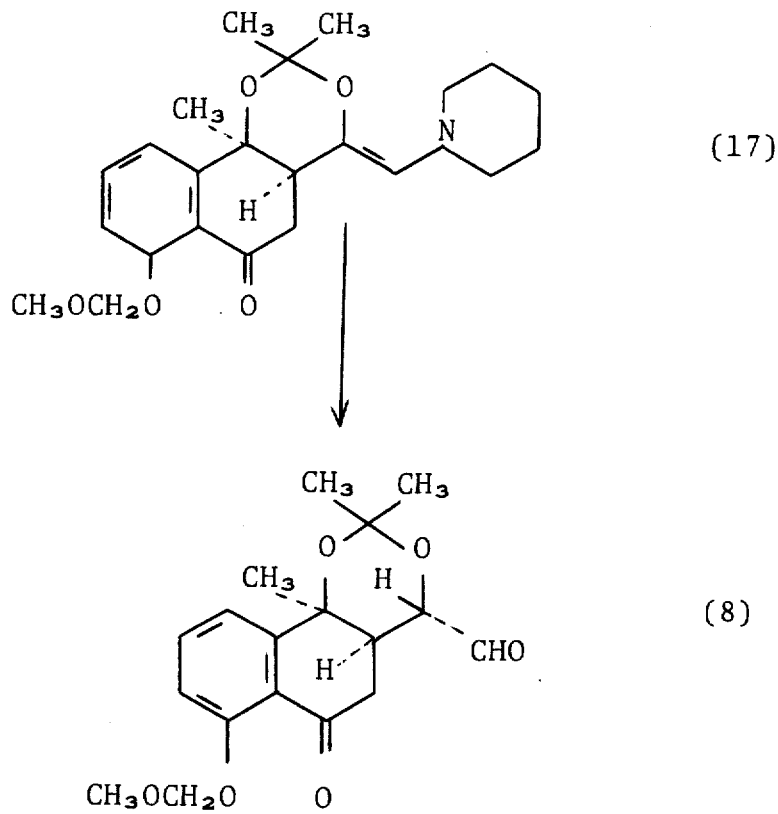

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

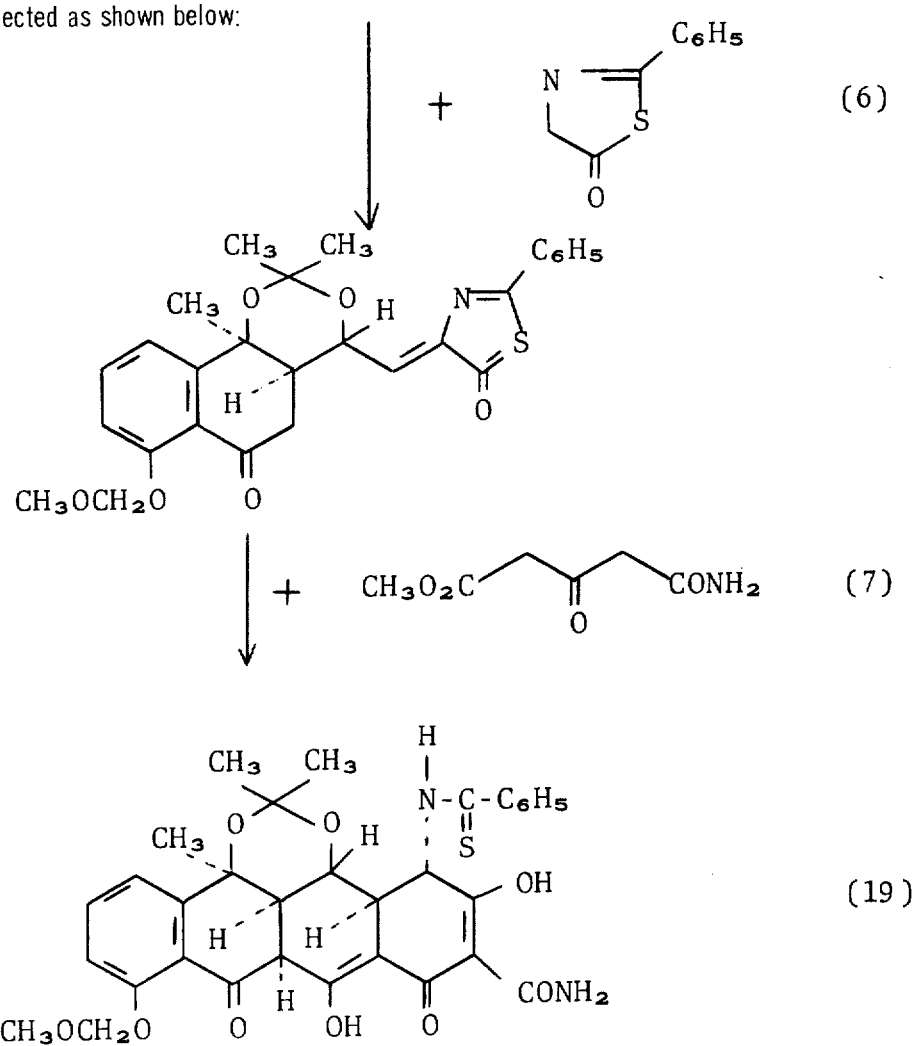

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

REMOVE METHOXYMETHYL ETHER

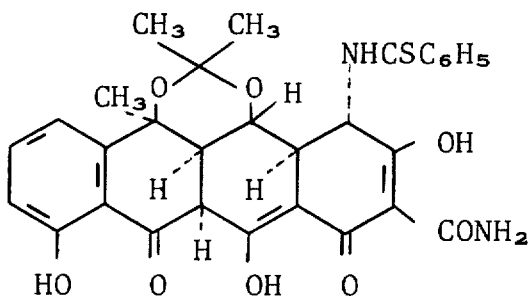

(20)

HYDROXYLATION
(KEY STEP)

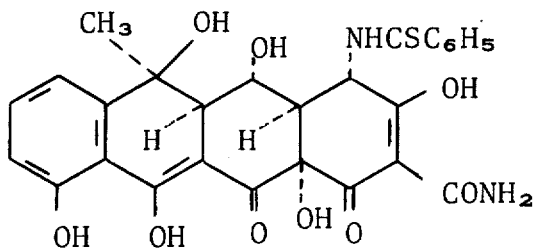

(21)

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

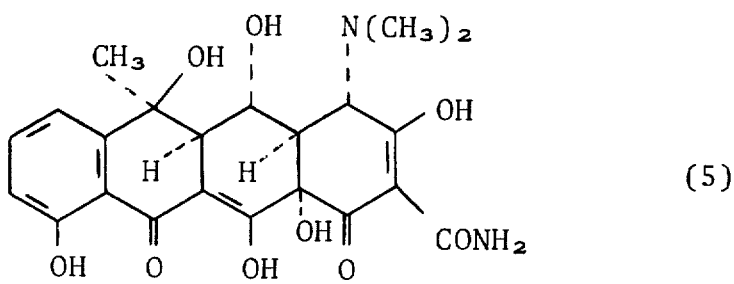

Column 14, lines 20-28, the formula should read as follows:

UNITED STATES PATENT AND TRADEMARK OFFICE
CERTIFICATE OF CORRECTION

PATENT NO. : 3,947,517
DATED : March 30, 1976
INVENTOR(S) : Hans H. Muxfeldt et al.

It is certified that error appears in the above-identified patent and that said Letters Patent are hereby corrected as shown below:

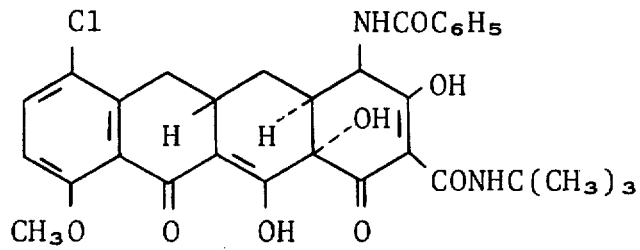

Signed and Sealed this

Seventh Day of December 1976

[SEAL]

Attest:

RUTH C. MASON
Attesting Officer

C. MARSHALL DANN
Commissioner of Patents and Trademarks